(12) United States Patent
Bezzek

(10) Patent No.: US 8,349,376 B1
(45) Date of Patent: Jan. 8, 2013

(54) ANTI-DEMENTIA REGIMEN

(76) Inventor: Mark S. Bezzek, Mill Spring, NC (US)

( * ) Notice: Subject to any disclaimer, the term of this patent is extended or adjusted under 35 U.S.C. 154(b) by 84 days.

(21) Appl. No.: 13/043,216

(22) Filed: Mar. 8, 2011

(51) Int. Cl.
| | |
|---|---|
| *A61K 39/9066* | (2006.01) |
| *A61K 36/45* | (2006.01) |
| *A61K 36/87* | (2006.01) |
| *A61K 36/16* | (2006.01) |
| *A61K 33/06* | (2006.01) |
| *A61K 33/04* | (2006.01) |
| *A61K 33/26* | (2006.01) |
| *A61K 31/122* | (2006.01) |
| *A61K 36/82* | (2006.01) |
| *A61K 36/889* | (2006.01) |
| *A61K 33/24* | (2006.01) |
| *A23L 1/302* | (2006.01) |
| *C07C 57/02* | (2006.01) |

(52) U.S. Cl. ........ 424/756; 424/732; 424/766; 424/752; 424/682; 424/702; 424/646; 424/94.1; 424/729; 424/727; 424/655; 426/72; 554/1

(58) Field of Classification Search .......................... None
See application file for complete search history.

(56) References Cited

U.S. PATENT DOCUMENTS

| | | | | |
|---|---|---|---|---|
| 4,897,388 | A * | 1/1990 | Malluche ...................... 514/167 |
| 5,798,392 | A * | 8/1998 | Moss ........................... 514/649 |
| 5,885,608 | A | 3/1999 | McEntee |
| 5,962,535 | A | 10/1999 | Miyamoto et al. |
| 5,994,322 | A | 11/1999 | Masuda et al. |
| 6,372,760 | B1 | 4/2002 | Kato et al. |
| 6,500,798 | B1 * | 12/2002 | Stanton et al. ............... 514/15.1 |
| 6,733,797 | B1 * | 5/2004 | Summers ...................... 424/728 |
| 6,953,794 | B2 * | 10/2005 | Wischik et al. ............. 514/224.8 |
| 6,964,969 | B2 * | 11/2005 | McCleary ...................... 514/283 |
| 7,935,365 | B2 * | 5/2011 | Dror et al. ..................... 424/456 |
| 2001/0036949 | A1 | 11/2001 | Coe et al. |
| 2003/0171385 | A1 * | 9/2003 | Alkon et al. .............. 514/263.31 |
| 2005/0234248 | A1 * | 10/2005 | Kossler et al. ................ 549/413 |
| 2006/0122270 | A1 * | 6/2006 | Henderson .................... 514/546 |
| 2006/0127505 | A1 * | 6/2006 | Haines et al. ................. 424/729 |
| 2006/0211721 | A1 * | 9/2006 | Roberts ........................ 514/276 |
| 2006/0257502 | A1 * | 11/2006 | Liu .............................. 424/682 |
| 2007/0060644 | A1 * | 3/2007 | Vander Jagt et al. ......... 514/475 |
| 2007/0116779 | A1 * | 5/2007 | Mazzio ......................... 424/539 |
| 2008/0213401 | A1 * | 9/2008 | Smith ........................... 424/657 |
| 2008/0214649 | A1 * | 9/2008 | Yu et al. ....................... 514/423 |
| 2009/0074677 | A1 * | 3/2009 | Marx et al. ..................... 424/45 |

FOREIGN PATENT DOCUMENTS

WO    WO 2009/009393 A2 *    1/2009

OTHER PUBLICATIONS

Bottiglieri et al., J Neurology Neurosurgery and Psychiatry 53, 1096-1098 (1990).*
Imagawa et al., Lancet 340, 671 (1992).*

* cited by examiner

*Primary Examiner* — Melenie McCormick
*Assistant Examiner* — Erin M Bowers

(57) ABSTRACT

A novel dietary supplement is featured which can benefit individuals suffering from various conditions such as nutritional deficiencies, vitamin deficiencies, aging, dementia/Alzheimer's disease, high blood pressure, high cholesterol, coronary artery disease, stroke and mental cognition.

1 Claim, No Drawings

ANTI-DEMENTIA REGIMEN

BACKGROUND OF THE INVENTION

The present invention features a novel dietary supplement which can benefit individuals suffering from various conditions such as nutritional deficiencies, vitamin deficiencies, aging, dementia/Alzheimer's disease, high blood pressure, high cholesterol, coronary artery disease, stroke and mental cognition.

The content of this patent application is presented solely for the purpose of being reviewed by the United States Patent and Trademark Office for patentability of the claimed novel dietary supplement. In accordance with the Dietary Supplement Health and Education Act of 1994 (DSHEA), Applicant asserts that statements made within this patent application have not been evaluated by the Food and Drug Administration. Further in accordance with DSHEA, Applicant asserts that the novel dietary supplement is not intended to diagnose, treat, prevent, mitigate or cure disease.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

The novel dietary supplement is referred to hereinafter as the "Formulation". In some embodiments, the Formulation comprises the following supplemental components: idebenone at about 180 mg; rhodiola at about 400 mg; gingko biloba at about 160 mg; thionine at about 400 mg; huperzine a at about 2 mg; coenzyme Q10 at about 400 mg; alpha lipoic acid at about 600 mg; melatonin at about 3 mg; omega 3 fatty acid at about 6000 mg; zinc carnosine at about 500 mg; magnesium at about 1000 mg; vitamin E (mixed tocotrienols gamma/delta) at about 1000 mg; N-acetyl cysteine at about 1200 mg; dehydroepiandrosterone (dhea) at about 100 mg; pregnenolone at about 60 mg; niacin at about 1000 mg; phosphotidylserine docasahexanenoic acid at about 300 mg; vitamin B12 at about 2000 mg; vitamin B6 at about 200 mg; iron at about 18 mg; vinpocetine at about 40 mg; phospholipid grapeseed extract at about 300 mg; blueberry extract at about 300 mg; acetyl l-carnitine arginate 900 mg; SENSORIL® ashwagandha extract at about 250 mg; uridine 5 monophosphate at about 100 mg; pycnogenol® (French maritime pine bark extract) at about 250 mg; L-alpha-glycerylphosphorylcholine at about 1500 mg; curcumin at about 8 gms; coconut oil at about 1000 mg; astaxanthin at about 20 mg; chromium picolinate at about 1200 mg; carnosine at about 3000 mg; n-acetyl-tyrosine at about 1500 mg; phenylalanine at about 1500 mg; quercetin at about 150 mg; inositol hexanicotinate at about 1000 mg; dimethylethanolamine (DMAE) at about 100 mg; s-adenosylmethionine at about 400 mg; riboflavin B2 at about 200 mg; thiamine B1 at about 50 mg; selenium (as L-selenomethionine sodium selenite) at about 200 mg; colostrum at about 4000 mg; lecithin (26% phosphaticylcholine) at about 300 mg; vitamin D2 at about 8000 IU.

In some embodiments, less than 10 of any supplemental components are removed from the Formulation. In some embodiments, less than 5 of any supplemental components are removed from the Formulation.

In some embodiments, the Formulation is administered to a human patient once a day. In some embodiments, the Formulation is administered to a human patient once a week.

The Formulation may be a solid tablet, granule, syrup or liquid form. One of ordinary skill would be able to prepare an appropriate form of the Formulation.

As used herein, the term "about" refers to plus or minus 10% of the referenced number. For example, the administration of uridine 5 monophosphate at "about 100 mg" means that uridine 5 monophosphate can be administered at 90 mg up to 110 mg.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A formulation comprising the following supplemental components:
    (a) idebenone at about 180 mg;
    (b) rhodiola at about 400 mg;
    (c) gingko biloba at about 160 mg;
    (d) thionine at about 400 mg;
    (e) huperzine a at about 2 mg;
    (f) coenzyme Q10 at about 400 mg;
    (g) alpha lipoic acid at about 600 mg;
    (h) melatonin at about 3 mg;
    (i) omega 3 fatty acid at about 6000 mg;
    (j) zinc carnosine at about 500 mg;
    (k) magnesium at about 1000 mg;
    (l) vitamin E (mixed tocotrienols gamma and delta) at about 1000 mg;
    (m) n-acetyl cysteine at about 1200 mg;
    (n) dehydroepiandrosterone (dhea) at about 100 mg;
    (o) pregnenolone at about 60 mg;
    (p) niacin at about 1000 mg;
    (q) phosphotidylserine docasahexanenoic acid at about 300 mg;
    (r) vitamin B12 at about 2000 mg;
    (s) vitamin B6 at about 200 mg;
    (t) iron at about 18 mg;
    (u) vinpocetine at about 40 mg;
    (v) grapeseed extract at about 300 mg;
    (w) blueberry extract at about 300 mg;
    (x) acetyl l-carnitine arginate 900 mg;
    (y) ashwagandha extract at about 250 mg;
    (z) uridine 5 monophosphate at about 100 mg;
    (aa) French maritime pine bark extract at about 250 mg;

(bb) l-alpha-glycerylphosphorylcholine at about 1500 mg;
(cc) curcumin at about 8 gms;
(dd) coconut oil at about 1000 mg;
(ee) astaxanthin at about 20 mg;
(ff) chromium picolinate at about 1200 mg;
(gg) carnosine at about 3000 mg;
(hh) n-acetyl-tyrosine at about 1500 mg;
(ii) phenylalanine at about 1500 mg;
(jj) quercetin at about 150 mg;
(kk) inositol hexanicotinate at about 1000 mg;
(ll) dimethylethanolamine (DMAE) at about 100 mg;
(mm) s-adenosylmethionine at about 400 mg;
(nn) riboflavin B2 at about 200 mg;
(oo) thiamine B1 at about 50 mg;
(pp) selenium at about 200 mg;
(qq) colostrum at about 4000 mg;
(rr) lecithin (26% phosphaticylcholine) at about 300 mg;
(ss) vitamin D2 at about 8000 IU.

\* \* \* \* \*